United States Patent
Bybee et al.

(10) Patent No.: US 6,843,357 B2
(45) Date of Patent: Jan. 18, 2005

(54) TWO-AXIS ROBOT FOR SPECIMEN TRANSFER

(75) Inventors: Thomas L. Bybee, Omaha, NE (US); Chris Harvey, Peterborough (CA); Sheri Kime, Peterborough (CA); Dave Murphy, Goodwood (CA); Greg Rothman, Omaha, NE (US); Steve Wright, Peterborough (CA)

(73) Assignee: Cardinal Health 301, Inc., San Diego, CA (US)

( * ) Notice: Subject to any disclaimer, the term of this patent is extended or adjusted under 35 U.S.C. 154(b) by 0 days.

(21) Appl. No.: 10/627,415

(22) Filed: Jul. 25, 2003

(65) Prior Publication Data

US 2004/0094385 A1 May 20, 2004

(Under 37 CFR 1.47)

Related U.S. Application Data

(60) Provisional application No. 60/398,893, filed on Jul. 26, 2002.

(51) Int. Cl.[7] .............................................. B65G 47/00
(52) U.S. Cl. ................................ 198/345.3; 198/468.2; 198/465.1; 414/222.06; 414/225.01; 414/226.02; 422/65; 436/47

(58) Field of Search .......................... 198/345.3, 465.1, 198/468.2; 414/222.06, 226.05, 225.01, 226.02; 422/65; 436/47, 48

(56) References Cited

U.S. PATENT DOCUMENTS

| 4,084,684 A | * | 4/1978 | Skinner, II ................ 198/468.2 |
| 4,411,576 A | * | 10/1983 | Smith et al. ........... 414/225.01 |
| 4,927,545 A | * | 5/1990 | Roginski ...................... 436/48 |
| 4,982,553 A | * | 1/1991 | Itoh ........................ 198/465.1 |
| 5,351,801 A | * | 10/1994 | Markin et al. ........... 198/465.1 |
| 5,417,922 A | * | 5/1995 | Markin et al. ................ 422/65 |
| 6,177,050 B1 | * | 1/2001 | Bybee et al. ................. 422/65 |

* cited by examiner

Primary Examiner—Joseph Valenza

(57) ABSTRACT

A two-axis robot includes a vertical tubular post mounted for rotation about its vertical axis, with a vertically slidable shaft extending through the post. An arm on the upper end of the post projects radially outward and has a gripper assembly thereon with operable jaws for gripping a specimen tube. The robot is positioned between two reference locations, for retrieving a specimen tube from one reference location and transferring it to the other. The reference locations are located along a circle circumscribed by a central vertical axis of the gripper jaws as they swing about the rotational axis of the post.

15 Claims, 2 Drawing Sheets

TWO-AXIS ROBOT FOR SPECIMEN TRANSFER

CROSS-REFERENCES TO RELATED APPLICATIONS

This application claims the benefit of U.S. Provisional Application Ser. No. 60/398,893, filed Jul. 26, 2002.

STATEMENT AS TO RIGHTS TO INVENTIONS MADE UNDER FEDERALLY SPONSORED RESEARCH AND DEVELOPMENT (Not applicable)

BACKGROUND OF THE INVENTION (1) Field of the Invention

The present invention relates generally to Cartesian robots used in conjunction with an automated clinical laboratory conveyor system, and more particularly to an improved two-axis robot for transferring specimen tubes from one location to another.

(2) Background Information

Clinical laboratory testing has changed and improved remarkably over the past 80 years. Initially, tests or assays were performed manually and generally utilized large quantities of serum, blood or other materials and/or body fluids. As mechanical technology developed in the industrial work place, similar technology was introduced into the clinical laboratory. With the introduction of new technology, methodologies were also improved in an effort to improve the quality of the results produced by the individual instruments, and to minimize the amount of physical specimen required to perform a particular test.

Instruments have been developed to increase the efficiency of testing procedures by reducing turnaround time and decreasing the volumes necessary to perform various assays. Robotic engineering has evolved to such a degree that various types of robots have been applied in the clinical laboratory setting.

The main focus of prior art laboratory automation relied on the implementation of conveyor systems to connect areas of a clinical laboratory. Known conveyor systems in the laboratory setting utilize separate conveyor segments to move specimens from a processing station to a specific laboratory work station. In order to obtain cost savings, one typical scenario called for specimens to be sorted manually and grouped together in a carrier rack to be conveyed to a specific location. In this way, a carrier would move a group of 5–20 specimens from the processing location to the specific work station for the performance of a single test on each of the specimens within the carrier rack.

With the development of new and improved automatic conveyor systems for laboratories and other environments, it is possible to select, track, and convey individual specimens throughout a laboratory for a variety of different testing, while maintaining a priority system for certain types of testing or special urgent requests for a time-specific response. These new automated conveyor systems are of various types and design, but the inventors herein have found that a dual conveyor system, using a pair of parallel conveyor tracks circulating throughout a laboratory, provides the greatest flexibility and versatility. The integration of various track devices with software directing the operation of the conveyor system and the various automated testing stations, has improved both the speed and capability of automated conveyor systems in recent years.

Track devices form the physical interface between the specimen samples in carriers being directed throughout the system, while the Laboratory Automation System (LAS) database provides direction for the system through its command and control features. The LAS and the various track devices work in combination to direct, manage and track all specimens throughout the system.

With the development of robotics to assist in the laboratory setting, the three-axis Cartesian robot has been the conventional device installed to load and unload specimen tubes in specimen carriers. These three-axis robots identify the X and Y coordinates of the specimen tube location in a carrier and then grip the tube and raise and lower the tube into the carrier, along the Z axis.

While Cartesian robots are adequate to perform this task, in the case of a carrier located at a predetermined position along a straight conveyor track, the need for the expensive Cartesian robot is less necessary. The inventors herein have found that a simple two-axis robot can perform the identical function, at a reduced initial cost, and with the attendant lower costs of maintenance and repair of a less complicated device.

BRIEF SUMMARY OF THE INVENTION

It is therefore a general object of the present invention to provide an improved two-axis robot for loading and unloading specimen tubes from a carrier on a conveyor of an automated conveyor system.

These and other objects will be apparent to those skilled in the art.

The two-axis robot of the present invention includes a vertical tubular post mounted for rotation about its vertical axis, with a vertically slidable shaft extending through the post. An arm on the upper end of the post projects radially outward and has a gripper assembly thereon with operable jaws for gripping a specimen tube. The robot is positioned between two reference locations, for retrieving a specimen tube from one reference location and transferring it to the other. The reference locations are located along a circle circumscribed by a central vertical axis of the gripper jaws as they swing about the rotational axis of the post.

BRIEF DESCRIPTION OF THE SEVERAL VIEWS OF THE DRAWING

The preferred embodiment of the invention is illustrated in the accompanying drawings, in which similar or corresponding parts are identified with the same reference numeral throughout the several views, and in which.

DETAILED DESCRIPTION OF THE INVENTION

Figure 1:
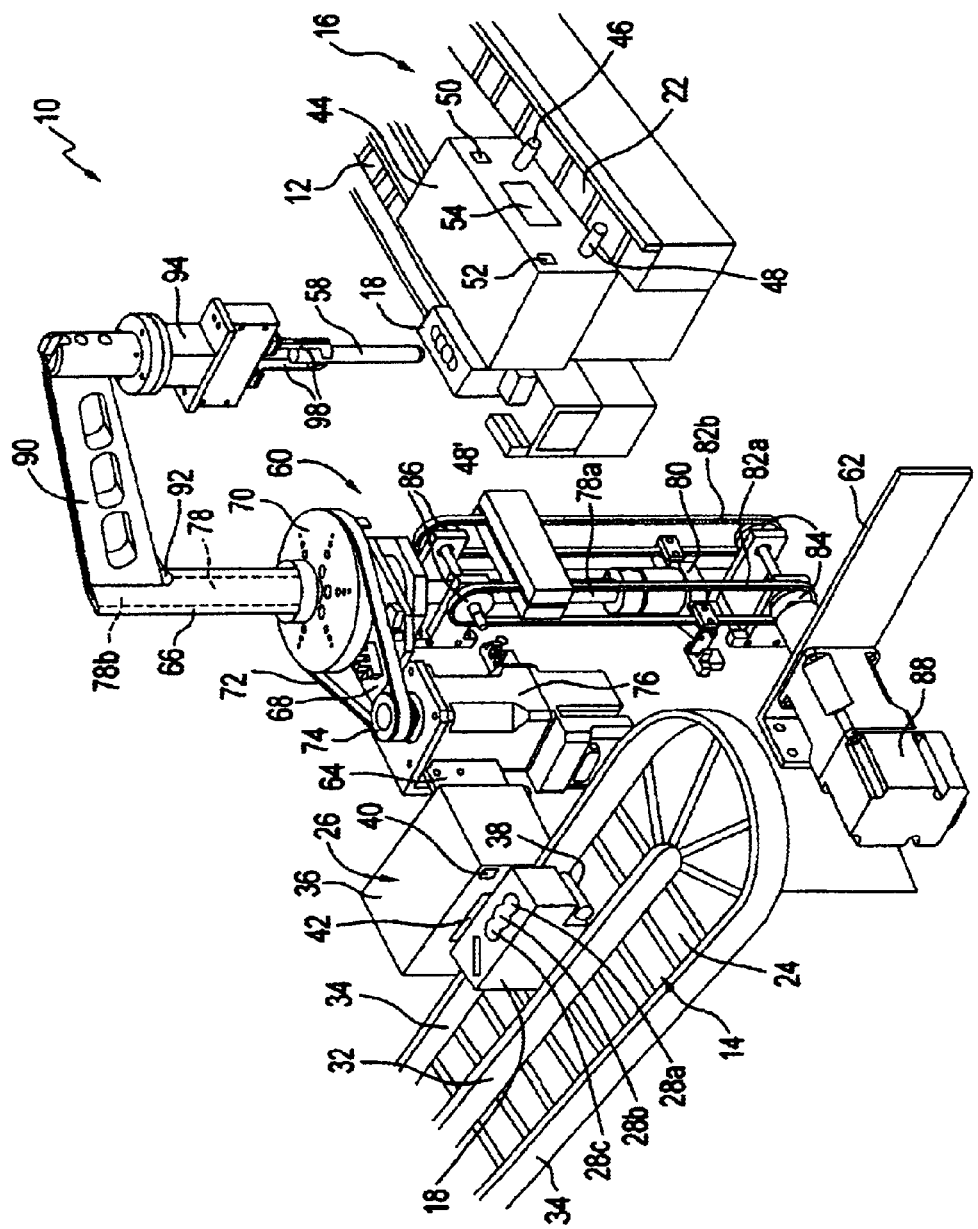
FIG. 1 is a perspective view of a two-axis robot of the present invention installed between a loading track and a conveyor track of an automated laboratory system.

Referring now to the drawings, in which similar or corresponding parts are identified with the same reference numeral, and more particularly to FIG. 1, the two-axis robot of the present invention is designated generally at 10, and is shown installed between a conventional conveyor 12 and a loading station conveyor 14 of an automated conveyor transport system. Preferably, conveyor 12 is one track of a dual-track conveyor system 16, with the capability for transferring a specimen carrier 18 between its dual tracks 12 and 22.

Figure 2:
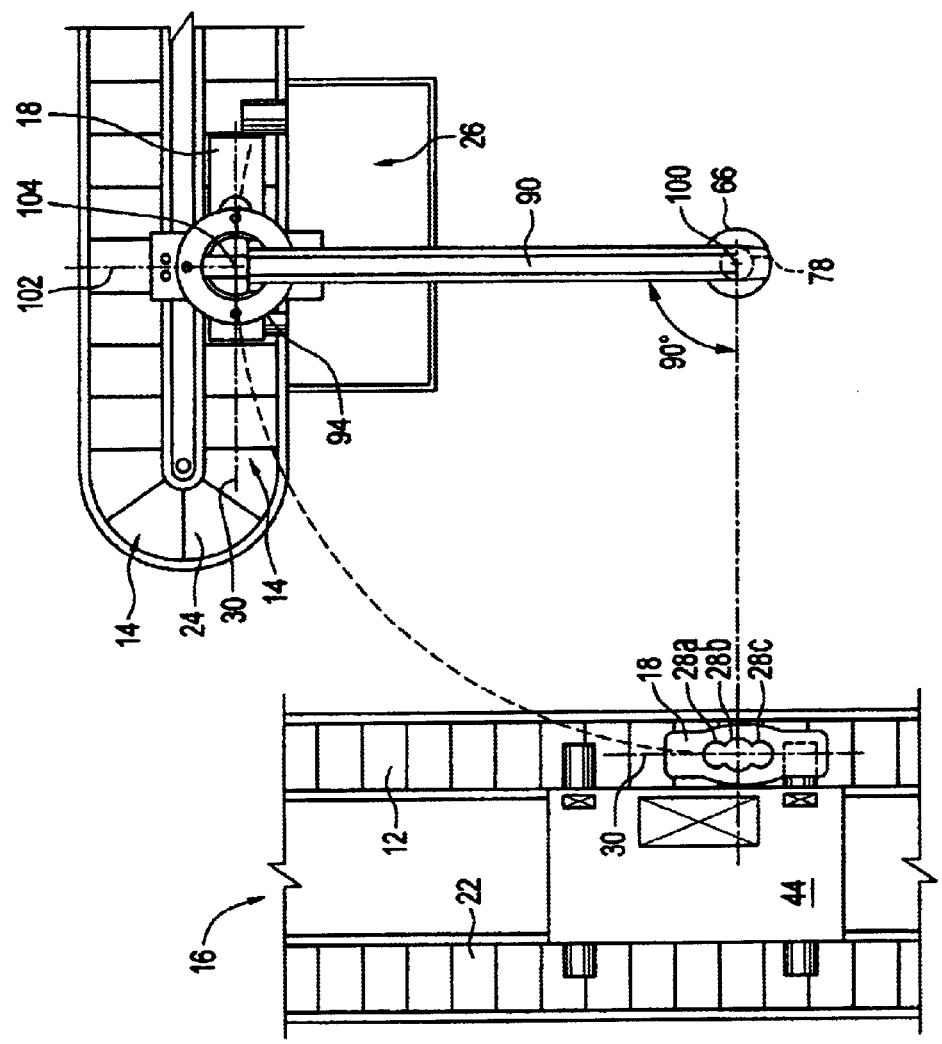
FIG. 2 is top plan view of the robot and tracks shown in FIG. 1.

Loading conveyor 14 includes a continuous loop table top chain 24, known in the art, which continuously circulates specimen carriers 18 around the loop. A queue 26 is installed adjacent one "run" of conveyor 14, to selectively stop a carrier 18 in a predetermined position on conveyor 14. Each carrier 18 is formed of a generally rectangular body having a series of three apertures 28a, 28b, and 28c formed in the top surface and extending downwardly into the body of the carrier. As shown in FIG. 2, apertures 28a, 28b and 28c are of different diameters and overlap one another. However, each aperture has a central axis located along a longitudinal centerline 30 of carrier 18, with the axes of the outward two apertures 28a and 28c spaced a uniform distance from the central aperture 28b. In the example shown in FIGS. 1 and 2, this distance is 0.404 inches.

A pair of elongated guide rails 32 and 34 are disposed along the length of conveyor 14 on opposing sides of the chain 24 to guide specimen carriers 18 therebetween. Queue 26 includes a housing 36 positioned adjacent on run of conveyor 14. A retractable shaft 38 extends transversely outwardly from housing 36 and projects over conveyor 14 to restrain a specimen carrier 18 from passing by shaft 38. A sensor 40 is positioned adjacent shaft 38 to detect the presence of a specimen carrier 18 at the shaft. A bar code scanner 42 on queue 26 scans the bar code label (not shown) on the side of specimen carrier 18 to identify the specimen carried by that carrier.

As discussed above, track 16 is a dual-lane system with a pair of generally parallel, closed loop conveyors 12 and 22. A dual-sided queue 44 is installed between conveyors 12 and 22 to selectively stop and scan specimen carriers 18 on both conveyors. As shown in FIG. 1, queue 44 includes an upstream and a downstream retractable shaft 46 and 48, respectively, for selectively restraining a specimen carrier 18. Sensors 50 and 52, adjacent each of shafts 46 and 48, respectively, detect the presence of a carrier 18 at the respective shafts. A bar code scanner 54 adjacent the downstream shaft 48, scans a bar code label on the side of a carrier 18 to read identification information from the carrier. Although not seen in FIG. 1, the opposing side of queue 44, adjacent conveyor 12, has identical shafts 46' and 48', sensors 50' and 52' and scanner 54'.

A command module 56 is shown in schematic form in FIG. 1, and includes a processor that communicates with the Laboratory Automation System (LAS) to receive instructions for the identification, tracking and processing of each specimen in the system. Command module 56 is electrically connected to each item of hardware in the automated conveyor system to command and control the entire system. Thus, queue 26, queue 44 as well as two-axis robot 10 of the present invention are all electrically interconnected with command module 56, although these connections are not specifically identified in the drawings. From the moment a specimen within a specimen tube 58 is first loaded into a carrier 18 on loading track 14, it is automatically identified, tracked and forwarded to various clinical instruments for processing.

Referring once again to FIG. 1, robot 10 includes a frame 60 for supporting the robot in relation to tracks 14 and 16. While not absolutely necessary, it is preferred that frame 60 be connected to a both tracks 14 and 16, to maintain absolute positioning reference with each track. This may be accomplished in a number of ways, including connecting beams 62 and 64.

Robot 10 includes a vertical post 66 mounted to a base plate 68 for rotation about its own vertical axis. A disk 70 mounted to post 66 has a drive belt 72 extending around the perimeter to rotate the disk, and thereby rotate post 66 on its vertical axis. Drive belt 72 extends around a drive pulley 74 connected to a motor 76, for selective movement of the disk 70 in either the clockwise or counter-clockwise directions. Motor 76 is electrically connected to command module 56 to receive instructions for the rotation of post 66.

Post 66 is a tubular member, and has an elongated shaft 78 extending therethrough for vertical slidable movement within the post 66. A lower end 78a of shaft 78 projects downwardly out of the bottom of base plate 68 and is connected to a drive plate 80 operable to move the shaft vertically through post 66. Drive plate 80 is connected between a pair of vertically oriented, continuous loop belts 82a and 82b for vertical movement with one run of each belt. Belts 82a and 82b extend around drive pulleys 84 at a lower end and idler pulleys 86 at an upper end. A motor 88 selectively drives drive pulleys 84 in each direction, to thereby raise and lower shaft 78 within post 66.

An arm 90 is mounted to the upper end 78b of shaft 78 and projects radially outwardly therefrom through a slot 92 in post 66. A gripper assembly 94 is mounted on the outward end 90a of arm 90 and depends vertically therefrom. Gripper assembly includes a housing 96 with a pair of depending, operable jaws 98. Jaws 98 are operable to move towards and away from one another on housing 96, to thereby grip or release a specimen tube 58 therebetween. Jaws 98 are oriented vertically and parallel to a vertical axis, to thereby grip the vertically oriented tube 58.

Referring now to FIG. 2, it can be seen that arm 90 swings about axis 100 of post 66 and shaft 78. The longitudinal axis 102 of arm 90 forms a radial extending from axis 100 and intersects the vertical axis 104 of gripper assembly 94 and the center axis between jaws 98 (shown in FIG. 1). Although loading track 16 is shown in the drawings oriented perpendicularly to conveyor track 16, this is not a requirement of the invention. Rather, the orientation of each track 14 and 16 must be perpendicular to a radial extending from vertical axis 100 of post 66, such that the centerline of a specimen carrier 18 on the respective track is oriented perpendicularly to a radial of axis 100. In addition, queues 26 and 44 must be positioned along the respective tracks 14 and 16 so that a specimen carrier 18 is stopped with central aperture 28b aligned with a radial of axis 100.

Because the specimen carriers 18 of the preferred embodiment of the invention have more than one aperture 28, and thus more than one possible location for a specimen tube 58, the positioning of carrier 18 perpendicular to arm 90 and a radial of axis 100 with the central aperture aligned with the same radial, will position apertures 28a and 28c about 0.007 inches from the centerline 30 of carrier 18. It has been found that this is sufficiently close to perpendicular to the radial to permit the jaws of the arm 90 to retrieve a specimen tube from either of apertures 28a or 28c. However, the length of arm 90 is determined by the amount of deviation that may be satisfactorily accounted for by the gripper assembly 94. In the embodiment shown in these drawings, arm 90 must have a length of at least 9.431 inches to achieve a maximum deviation of 0.007 inches from the centerline of a specimen carrier 18 stopped at either queue 26 or queue 44.

In operation, two-axis robot 10 may be used to load a specimen tube from loading track 14 to conveyor system track 16, for processing. A specimen tube 58 with a specimen sample is inserted in an appropriate one of apertures 28a, 28b or 28c on specimen carrier 18 on loading track 14. As the carrier 18 is stopped at queue 26 by retractable shaft 38, its presence is detected by sensor 40 and transmitted to command module 56. The command module will then instruct scanner 42 on queue 26 to scan the bar code label on the carrier 18 and transmit the identification data back to the command module 56. The processor in command module 56 will communicate with the LAS to determine any clinical testing that is required for that specimen.

Assuming that testing needs to be done, command module 56 will instruct the robot 10 to swing arm 90 to a location with the jaws 98 centered over the correct aperture 28a, 28b or 28c on carrier 10 on track 14. This location may be described as the first reference location, and must be located along the circle circumscribed by the central vertical axis 104 of gripper assembly jaws 98 as the arm 90 is rotated on the post 66. The jaws 98 are operated to close and grip the tube 58, and then the shaft 78 of robot 10 is raised, to lift the tube 58 from the carrier 18 on track 14. Arm 90 is rotated to align with a predetermined aperture 28a, 28b or 28c on a specimen carrier 18 on conveyor track 12. This location may be described as a second reference location, and is also along the circle circumscribed by the gripper jaw central vertical axis 104. Shaft 78 is lowered and tube 58 is inserted in the carrier 18 on conveyor track 12.

If the bar code on carrier 18 on track 12 has not already been scanned, it will be scanned at this time, and the identification information for the particular sample transmitted to the command module 56. Command module 56 then determines where the carrier must be directed on the conveyor system track 16, and downstream shaft 48' is retracted to send carrier 18 on its way.

While the operation described above was for the purpose of loading a specimen onto the conveyor track 16, it should be understood that robot 10 could be used in many other situations as well. For example, the robot could be used for removing a specimen from the system, after processing. The robot 10 could also be used at specific clinical instruments to bring a test tube directly to the instrument for testing, and then returning the specimen to the carrier.

Whereas the invention has been shown and described in connection with the preferred embodiment thereof, many modifications, substitutions and additions may be made which are within the intended broad scope of the appended claims.

What is claimed is:

1. A two-axis robot for transferring a specimen container from a first reference location on a first conveyor to a second reference location spaced from the first conveyor, comprising:
   a frame for supporting the robot;
   a vertically oriented post having a vertical rotational axis, said post mounted for selective rotation on said frame;
   a first motor mounted on the frame, connected to the post for selectively rotating the post in first and second directions on the rotational axis;
   said frame connected to said first conveyor to maintain the first conveyor at a predetermined distance relative to the post rotational axis;
   a queue on said first conveyor, for selectively retaining a specimen container on the first conveyor in a first reference location;
   a second reference location spaced from the first conveyor, for receiving a specimen container from the first reference location, said frame connected to the second reference location to maintain the second reference location at a predetermined distance from the post rotational axis;
   said first and second reference locations spaced an equal distance from the post rotational axis;
   a vertical shaft slidably mounted on said post for selective vertical movement;
   a second motor on said frame, connected to the shaft for selectively raising and lowering the shaft on said post;
   an arm mounted on an upper end of said shaft and extending radially outwardly from the shaft to an outer end located at a distance to extend over the first and second reference locations;
   a gripper assembly mounted on the outer end of the arm, with a pair of operable jaws depending therefrom;
   said jaws oriented generally vertically and parallel one another, and operable between an open position with both jaws spaced equidistant outwardly from a vertical central axis, and a closed position in gripping engagement on opposite sides of a specimen container;
   said first and second reference locations located along a circle circumscribed by the vertical central axis of the gripper assembly jaws as the arm is rotated on the post rotational axis; and
   a command and control module with a processor electrically connected to the first and second motors and the queue, for controlling the operation of the robot to move a specimen container between the first and second reference locations.

2. The two-axis robot of claim 1, wherein said specimen container is a generally cylindrical specimen tube.

3. The two-axis robot of claim 2, wherein said first reference location is a first vertical aperture in the top of a generally rectangular specimen carrier, the specimen carrier having a horizontal longitudinal centerline with a central axis of the aperture located along the centerline.

4. The two-axis robot of claim 3, wherein said first conveyor is oriented such that the specimen carrier centerline is perpendicular to a radial from the post rotational axis.

5. The two-axis robot of claim 4, wherein said specimen carrier includes a plurality of apertures formed in the top, each of the apertures having a vertical axis located along the carrier centerline, and wherein said first aperture is generally center among the plurality of apertures.

6. The two-axis robot of claim 5, wherein said plurality of apertures in the specimen carrier includes a forward-most aperture and a rearward-most aperture, said forward-most and rearward-most aperture vertical axes spaced equidistant and at a predetermined distance from the vertical axis of the first aperture.

7. The two-axis robot of claim 6, wherein said first and second reference locations are spaced a distance from the post rotational axis such that the vertical axes of the forward-most and rearward-most apertures are no more than 0.007 inches from the circle circumscribed by the gripper jaws central vertical axis as it rotates about the post rotational axis.

8. The two-axis robot of claim 7, wherein said second reference location is a first vertical aperture in the top of a generally rectangular specimen carrier, the specimen carrier carried on a second conveyor and having a horizontal longitudinal centerline with a central axis of the aperture located along the centerline.

9. The two-axis robot of claim 8, wherein said second conveyor is oriented such that the centerline of the specimen carrier thereon is perpendicular to a radial from the post rotational axis.

10. The two-axis robot of claim 9, wherein said specimen carrier on the second conveyor includes a plurality of apertures formed in the top, each of the apertures having a vertical axis located along the carrier centerline, and wherein said first aperture is generally center among the plurality of apertures.

11. The two-axis robot of claim 10, wherein said queue includes a retractable shaft operable between an extended position projecting across the first conveyor to stop a specimen carrier thereon, and a retracted position clear of the first conveyor to permit movement of the carrier thereby on the first conveyor.

12. The two-axis robot of claim 11, wherein said queue includes a motor for selectively extending and retracting the retractable shaft, said motor electrically connected to the command and control processor and responsive to instruction therefrom to extend and retract the retractable shaft.

13. The two-axis robot of claim 12, wherein said queue further includes a sensor adjacent the retractable shaft to detect the presence of a specimen carrier at said retractable shaft, said sensor electronically connected to the command module processor for transmitting detection information thereto.

14. The two-axis robot of claim 13, wherein said queue further includes a scanner in said housing oriented to scan a specimen carrier restrained by the retractable shaft, to collect identification data therefrom, said scanner electrically connected to the command module and adapted to transmit identification data to the command module.

15. The two-axis robot of claim 14, wherein said second reference location further includes a scanner oriented to scan a specimen carrier at the second reference location, to collect identification data therefrom, said scanner electrically connected to the command module processor and adapted to transmit identification data to the command module.

* * * * *